US010639429B2

(12) United States Patent
Haindl et al.

(10) Patent No.: US 10,639,429 B2
(45) Date of Patent: May 5, 2020

(54) SYRINGE FOR SEQUENTIAL INJECTION OF SUBSTANCES

(71) Applicant: SFM MEDICAL DEVICES GMBH, Wächtersbach (DE)

(72) Inventors: Hans Haindl, Wennigsen (DE); Markus Kehr, Biebergemund (DE)

(73) Assignee: Hans Haindl, Wennigsen (DE)

( * ) Notice: Subject to any disclaimer, the term of this patent is extended or adjusted under 35 U.S.C. 154(b) by 435 days.

(21) Appl. No.: 15/033,691

(22) PCT Filed: Nov. 13, 2014

(86) PCT No.: PCT/EP2014/074472
§ 371 (c)(1),
(2) Date: Aug. 23, 2016

(87) PCT Pub. No.: WO2015/071352
PCT Pub. Date: May 21, 2015

(65) Prior Publication Data
US 2016/0346481 A1 Dec. 1, 2016

(30) Foreign Application Priority Data

Nov. 14, 2013 (DE) ........................ 10 2013 112 521
Mar. 14, 2014 (DE) ........................ 10 2014 103 469

(51) Int. Cl.
*A61M 5/31* (2006.01)
*A61M 5/315* (2006.01)
(Continued)

(52) U.S. Cl.
CPC .......... *A61M 5/31596* (2013.01); *A61M 5/19* (2013.01); *A61M 5/282* (2013.01);
(Continued)

(58) Field of Classification Search
CPC .............. A61M 5/315; A61M 5/31596; A61M 5/31515; A61M 5/19; A61M 2005/1787;
(Continued)

(56) References Cited

U.S. PATENT DOCUMENTS 4,693,706 A   9/1987 Ennis, III
4,753,638 A * 6/1988 Peters ..................... A61M 3/00
                                                        604/212

(Continued)

FOREIGN PATENT DOCUMENTS

DE   1 961 166 A1   7/1970
DE   43 39 528 A1   6/1995
(Continued)

OTHER PUBLICATIONS

Non-English International Search Report dated Feb. 5, 2015 for Application No. PCT/EP2014/074472 with English translation.
(Continued)

*Primary Examiner* — Amber R Stiles
(74) *Attorney, Agent, or Firm* — Ladas & Parry LLP; Malcolm J. MacDonald

(57) ABSTRACT

A syringe for the injection of an active substance and for the secondary injection of a medium, the syringe having a cylindrical syringe body with a limiting wall provided in the distal region, which transitions into a neck, two mechanically connected plungers that are axially displaceable in the syringe body, and a first actuating element for mutual displacement of the plungers, wherein, prior to the injection of the active substance, the distal plunger and the limiting wall delimit a first volume that is filled with the active substance, and mutually facing inner surfaces of the plungers delimit a second volume that is filled with the medium, wherein the plungers are displaced as a mechanically coupled unit by the application of force of the first actuating
(Continued)

Figure 1:
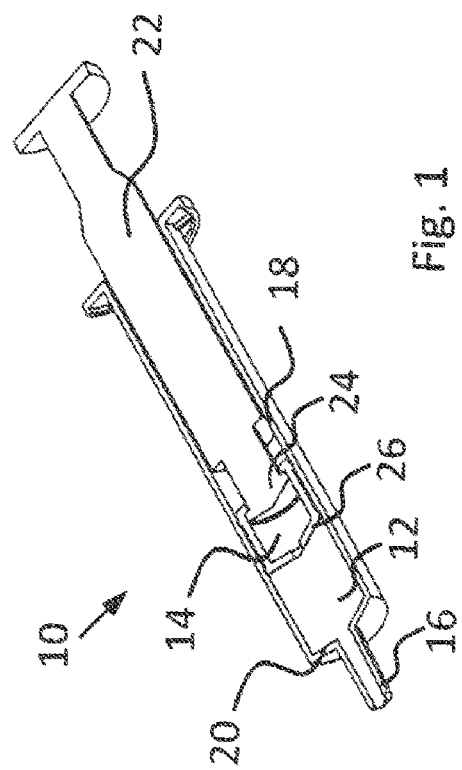

element in the direction of the limiting wall until the distal plunger comes to rest against the limiting wall or a stop.

17 Claims, 22 Drawing Sheets

(51) Int. Cl.
*A61M 5/19* (2006.01)
*A61M 5/28* (2006.01)
*A61M 5/178* (2006.01)

(52) U.S. Cl.
CPC .... *A61M 5/31511* (2013.01); *A61M 5/31515* (2013.01); *A61M 2005/1787* (2013.01)

(58) Field of Classification Search
CPC . A61M 5/31511; A61M 5/282; A61M 5/2066
USPC ........................................................ 604/231
See application file for complete search history.

(56) References Cited

U.S. PATENT DOCUMENTS

| | | | | |
|---|---|---|---|---|
| 5,102,388 A | * | 4/1992 | Richmond | A61M 5/31596 604/191 |
| 5,454,268 A | | 10/1995 | Kim | |
| 6,077,252 A | | 6/2000 | Siegel | |
| 6,270,482 B1 | * | 8/2001 | Rosoff | A61M 5/282 604/200 |
| 6,485,471 B1 | | 11/2002 | Zivitz et al. | |
| 7,011,650 B2 | * | 3/2006 | Rosoff | A61M 5/282 604/191 |
| 2012/0220950 A1 | * | 8/2012 | Carlyon | A61M 5/31596 604/191 |
| 2012/0265150 A1 | | 10/2012 | Frey et al. | |

FOREIGN PATENT DOCUMENTS

| | | |
|---|---|---|
| DE | 100 22 565 A1 | 11/2001 |
| DE | 603 14 018 T2 | 1/2008 |
| DE | 10 2009 051 863 B3 | 2/2011 |
| EP | 0 652 019 A1 | 5/1995 |
| WO | 2005/072644 A1 | 8/2005 |
| WO | 2010/051429 A1 | 5/2010 |
| WO | 2012/006555 A1 | 1/2012 |

OTHER PUBLICATIONS

Non-English International Preliminary Report on Patentability dated May 17, 2016 for Application No. PCT/EP2014/074472 with English translation.
Espacenet English abstract of EP 0 652 019 A1.
Espacenet English abstract of DE 10 2009 051 863 B3.
Espacenet English abstract of EP 0 654 280 A1 which corresponds to DE 43 39 528 A1.

* cited by examiner

SYRINGE FOR SEQUENTIAL INJECTION OF SUBSTANCES

This application is a 371 of PCT/EP2014/074472, filed on Nov. 13, 2014, which claims priority to German application number 10 2013 112 521.2, filed on Nov. 14, 2013, and German application number 10 2014 103 469.4, filed on Mar. 14, 2014.

The invention relates to a syringe for injection of an active substance, comprising a cylindrical syringe body with a limiting wall in the distal region, transitioning into a neck or having an opening via which the active substance can be delivered, two mechanically connected plungers that are axially displaceable in the syringe body, and a first actuating element for mutual displacement of the plungers, wherein, prior to the injection of the active substance, the distal plunger and the limiting wall are spaced from one another and the first volume that is formed thereby is filled with the active substance, wherein the plungers can be displaced as a mechanically coupled unit by the application of force of the first actuating element in the direction of the limiting wall until the distal plunger comes to rest against the limiting wall or a stop.

In various fields of medicine, once an active substance has been injected, it is sometimes necessary to inject another substance. This may be due to the fact that the active substance is very expensive and it is desirable for the quantity of substance still remaining in the dead space of an injection system, such as a butterfly cannula, to be used. For this purpose it is known, for example, to inject a saline solution following an initial injection.

Another reason for secondary injection may be that, for example in the case of catheters, which lie still for extended periods, the volume of the catheter must be flushed following administration of the active substance, either because the active substance such as blood could enter the catheter, or because the active substance is aggressive and could therefore damage the catheter material. Secondary injection is usually carried out by keeping a second syringe at the ready, and using this syringe for secondary injection once the active substance has been administered. This not only takes a considerable amount of time, since the second syringe must also be drawn back, it also involves microbiological risks, because every time syringes are changed, there is a risk that germs may enter.

U.S. Pat. No. 5,454,268 A describes a double plunger syringe comprising two coaxially arranged and reciprocally displaceable plungers which are biased against one another by a spring. To inject an active medium, the distal plunger is first moved against the spring force in the direction of a cannula neck. Once the distal plunger abuts the cannula neck, the inner plunger, which is retained by an additional spring element, is first pushed through the distal plunger to then enter into the cannula neck to displace any active medium located there.

Other syringes having a double plunger assembly for injecting a second medium, for example, or for mixing substances, are known from the prior art. For instance, EP 0 652 019 A1 discloses a syringe for mixing and administering a substance for injection. The syringe comprises a plunger having a stopper, which defines a volume in which an axially adjustable mixing plunger is disposed. The mixing plunger extends outward from a plunger rod which extends through the stopper.

A corresponding mixing device is also described by DE 1 961 166 A1, however in this case the mixing is performed by means of a plunger, which is arranged floatingly in the syringe body and which can be sealed via a valve.

A double plunger assembly with a floating plunger is also described in DE 10 209 051 863 B3. In this case, the floating, distally extending inner plunger divides the syringe into two chambers so that different fluids can be injected.

From DE 603 14 018 T2, a syringe assembly is known, in which a plunger rod from which two plungers extend can be displaced axially in a cylinder, which holds an active substance. Stationary stoppers for subdividing the volume of the cylinder are also provided.

Syringes having double plunger assemblies are structurally complex and are therefore rarely used in practice. Another disadvantage is that such syringes frequently must be prefilled with the active substance, in other words, they cannot be filled on site.

DE 43 39 528 A1 discloses a disposable syringe consisting of a plunger with a centrally extending projection and a sealing lip surrounding said projection peripherally, which rests against the syringe cylinder under radial tension, forming a tight seal. Active substance that collects between the sealing lip and the projection can be forced out by applying axial force to the plunger in the direction of the syringe connection by shifting the sealing lip in the direction of the projection.

The subject matter of DE 100 22 565 A1 is a telescoping plunger assembly.

The object of the present invention is to propose a syringe with which residual quantities of active substances can be easily injected from the syringe, and which does not necessarily have to be prefilled at the location where the active substance is produced. The syringe should also be designed for easy maintenance, so that it can be produced cost-effectively.

To solve the problem, the invention proposes a syringe for injection of an active substance, comprising a cylindrical syringe body with a limiting wall in the distal region, transitioning into a neck via which the active substance can be delivered, two mechanically connected plungers that are axially displaceable in the syringe body, and a first actuating element for mutual displacement of the plungers, wherein, prior to the injection of the active substance, the distal plunger and the limiting wall are spaced from one another and the first volume that is formed thereby is filled with the active substance, wherein the plungers can be displaced as a mechanically coupled unit by the application of three of the first actuating element in the direction of the limiting wall until the distal plunger comes to rest against the limiting wall or a stop, wherein the syringe is characterized in that when the plungers are a mechanically coupled unit, mutually facing inner surfaces of the plungers are spaced from one another, and the second volume that is thereby formed is filled with a medium for secondary injection, in that when the distal plunger abuts the limiting wall either the mechanical connection between the plungers can be automatically changed such that the proximal plunger is displaced in the direction of the distal plunger by a further application of axial force onto the first actuating element, or the mechanical connection between the plungers can be released manually and the proximal plunger can be displaced in the direction of the distal plunger by an axial displacement of a second actuating element guided by means of the first actuating element, wherein the displacement of the proximal plunger in the direction of the distal plunger causes the secondary injection medium to push through the distal plunger and/or to flow past the same.

According to the invention, a double plunger syringe is used for purposefully flushing an active medium from the dead volume of the syringe or from a cannula or catheter connected thereto. In this case, it is not necessary for the first volume, that is to say the region between the neck and the distally extending end face of the distal plunger, to be prefilled. Instead, the syringe can be filled with the active substance, i.e. a drug, on site. In addition, sterile air which can be used for flushing the syringe should be located as a medium between the plungers.

Due to the mechanical coupling between the plungers, the syringe can easily be filled with an active substance without the second volume that extends between the plungers, and thus the sterile air, escaping. During use, the unit consisting of the plungers is then displaced axially toward the neck by an axial application of force, in order to inject the active substance. Once the distal plunger abuts the neck or a limiting wall that transitions into the neck, or some other type of stop, the mechanical connection between the plungers is released so that the proximal plunger can then be displaced toward the distal plunger, with the result that the medium contained in the second volume, such as sterile air, is delivered via the distal plunger neck and thus via a cannula or a catheter. Cannula or catheter or any other tubing system is therefore flushed with the air. In this, it is immaterial if small amounts of air enter the body by venous application.

The obligatory mechanical coupling of the plungers, as opposed to floating plungers, ensures that a defined quantity of medium, in particular sterile air, is secondarily injected. Applications of a specific amount of force are not necessary for secondary injection, in contrast to double plunger designs in which the plungers are mutually spring biased in order to enable the successive movement first of the unit consisting of first and second plungers and then of the proximal plunger, as provided for by U.S. Pat. No. 5,454,268 A, without the possibility of a secondary injection.

In particular, the invention provides that the distal plunger is a hollow plunger having a distally extending base wall and a circumferential wall proceeding therefrom and forming a hollow cylinder with an edge region extending radially in sections along the longitudinal axis of the plunger, in particular a circumferential inwardly angled edge, which engages in a recess that receives the edge region in the outer side of the proximal plunger and extends spaced from at least the distal edge of the proximal plunger. Both the distal and proximal plungers are sealed peripherally against the inner wall of the syringe body to prevent the medium from escaping from the second volume, which extends between the plungers.

In this solution, the proximal plunger can be moved within the distal plunger in order to secondarily inject the medium.

Sterile air, which is used for secondary injection or for flushing, can be located in the second volume that is delimited by the plunger.

A configuration of this type also allows a medium to be drawn into the space between the plungers. This is possible when the proximal plunger is displaced toward the distal plunger to then draw the first actuating element back with the proximal plunger, thereby enlarging the volume between the plungers and allowing a medium to be drawn in. For this purpose, the distal plunger has a corresponding opening such as slit, which is designed to act as a valve.

To prevent the actuating element and thus the proximal plunger from being pulled out of the syringe body as they are being drawn back, a retention ring is provided in the syringe body for locking the proximal plunger in place once it reaches a starting position. During this drawing back, the distal plunger is moved along, so that the active substance can be drawn in at the same time.

To prevent relative movement between the plungers as the unit consisting of the plungers is being displaced axially up to the point at which the distal plunger abuts the neck or the limiting wall, it is provided that the plungers are interlocked, in particular by a projection which is provided in at least one of the plungers engaging in a matching recess in the other plunger. Alternatively, the plungers can be fixed to one another by a predefined amount of adhesive friction.

According to an alternative proposal, the plungers are mechanically coupled by means of axially extending spacer elements, which can be destroyed by an additional application of force in the direction of the neck once the distal plunger has reached the neck or the limiting wall. In this design, it is not possible for a medium such as sterile air to be drawn into the space that extends between the plungers. It must already be in place when the syringe is delivered. However, the active substance can be drawn in by drawing back the plunger unit from its initial position in which it abuts the neck or the limiting wall.

A syringe of this type can be used only once, because the spacer elements in the form of webs are destroyed after use.

A further embodiment provides for the distal plunger to be connected via an axially compressible, particularly bellows-type element, wherein the element is formed as a hollow body and is peripherally closed.

In this case, it is possible for the element to peripherally encompass the second volume or for the second volume to be enclosed between the hollow body and the syringe body.

The body, made of an elastic material, can transition distally into a section which forms the distal plunger. Proximally, the body is connected to the plunger rod and is sealed on the inside in relation to the syringe body. This area then performs the function of the first or proximal plunger when the medium for secondary injection is located between the outer side of the elastic body and the inner wall of the syringe body. If in contrast, the medium for secondary injection is encompassed by the body, the section of the plunger rod that delimits the inner space that is encompassed by the body forms the proximal or first plunger, along which the elastic body may also extend.

The region of the body made of elastic material, which connects the plungers, has the shape in cross-section, in the non-compressed state, of two arcuate sections that extend concave in relation to the syringe body, with the central section preferably extending parallel, at least in regions, to the longitudinal axis of the cylindrical syringe body. The cross-section of the body as viewed along the longitudinal axis is therefore smaller in the center region than in the end edge regions.

The particularly bellows-type body produces an elastic connection between the plungers. The syringe can be supplied with the medium such as sterile air to be secondarily injected already between the plungers, or filling can be carried out on site, if the medium will be absorbed by the body.

To fill the second volume, it is first necessary for the elastic, quasi spring-biased body that connects the plungers to be compressed, in order for the space that thereafter enlarges between the plungers as the proximal plunger is drawn back or as a result of an automatic relaxation of the body to then be filled with sterile air. By drawing the plunger back further, the active substance can then be drawn into the space between the neck and the distally extending end face of the distal plunger.

In the solutions described above, the distal plunger can be configured such that the intermediate space is filled with a medium, in particular sterile air, between the plungers, in other words, the medium can be suctioned in by the distal plunger. Independently of this, the distal plunger is configured such that, when the proximal plunger moves toward the distal plunger in the distal direction, the medium present in the intermediate space is delivered via the distal plunger. For this purpose, it is provided in particular that an opening is provided in the plunger, which is covered by a hydrophobic filter, for example. The sealing may also be effected by means of a membrane which is destroyed, for example, by movement of the proximal plunger toward the distal plunger. A connection can also be produced by a projection extending in the axial direction from the distal region of the syringe body, said projection forming an opening, or in the embodiment example, perforating a membrane that seals an opening.

If the plungers are connected to one another by an elastic body, the invention provides that, according to an inventive feature, when the secondary injection medium is injected, the proximal plunger can be prevented from sliding back. This can be accomplished, for example, by locking or clamping or frictional engagement preventing any backward movement as a result of the bias of the elastic body, which might otherwise result in blood being drawn.

The proximal plunger end/or the elastic body can be fixed in place, preferably by frictional engagement.

In particular, it is provided that a projection extending along the longitudinal axis of the syringe body proceeds outward from the proximal plunger, and can be fixed in the neck, in particular by frictional engagement, when the elastic body is in a compressed state, in the manner of a Luer's cone.

The invention thus also relates to a syringe for injection of an active substance, wherein two axially displaceable, mechanically connected plungers are provided in a syringe body, wherein the distal plunger is a hollow body or a portion thereof, and when the hollow body is in a compressed state, the proximal plunger is fixed in place, in particular by frictional engagement, by a projection that proceeds therefrom and extends in a neck of the syringe body. Thus, once injection has been completed and no force is acting on the proximal plunger, the proximal plunger cannot slide back.

In a further enhancement, the projection, which preferably has a spike-shaped or pin-shaped geometry, or a star-shaped or cruciform geometry in cross-section, can penetrate the elastic hollow body when the hollow body is compressed, thereby producing a connection between the second volume encompassed by the hollow body and the neck.

So that a flow of the secondary injection medium through the neck is not inhibited by the projection extending therein, it is preferably provided that the projection has, in its outer surface, at least one depression, such as a groove, extending longitudinally along the projection. In particular, it is provided that a plurality of depressions such as grooves extending in the longitudinal direction are distributed uniformly around the periphery of the projection.

Another proposal for preventing the proximal plunger from sliding back as a result of the relaxation of the elastic hollow body following injection of the secondary injection medium involves locking the hollow body and/or the proximal plunger in place. Also, or additionally, sliding backward can be prevented by the negative pressure prevailing in the space surrounding the elastic body, as this prevents the elastic body from expanding.

All of these measures ensure that after secondary injection, the proximal plunger is prevented from sliding back so that blood from the body in which the syringe is placed cannot be drawn.

The invention is further characterized in that the proximal plunger forms the distal portion of a plunger rod which forms the first actuating element, and sections of which preferably abuts the inside of the cylinder body. In this respect, design solutions that are known from other plunger syringes are proposed.

According to an alternative solution, it is provided that the end surface region of the distal plunger is formed by a plunger rod embodied as at least partially hollow, in which the proximal plunger can be axially displaced by means of the second actuating element, which can be displaced in and is guided by the plunger rod. In this case, the second actuating element is fixed to the first actuating element forming a unit during the axial displacement of the plunger, and once the distal plunger has reached the neck or the limiting wall, the second actuating element can be displaced in the axial direction in relation to the first actuating element, toward the neck.

In particular, it is provided that the second actuating element extends in the interior of the first actuating element and has a section that extends through the circumferential wall of the first actuating element, which section can be displaced, during the axial displacement of the second actuating element in the direction of the neck, in an axially extending longitudinal slit in the circumferential wall of the first actuating element.

The invention is also characterized by the use of a syringe having at least some of the aforementioned features or a selected combination of these for injection of an active substance and for secondary injection of a medium.

Additional details, advantages and features of the invention result not only from the claims, the features specified therein—alone and/or in combination—but also from the following description of preferred embodiments.

Figure 2:
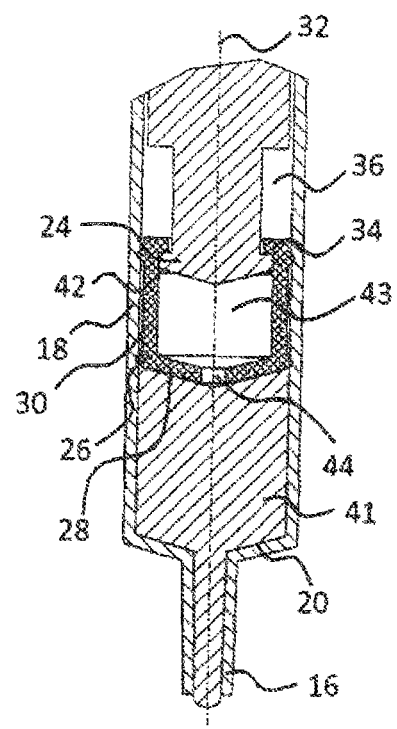
Figure 3:
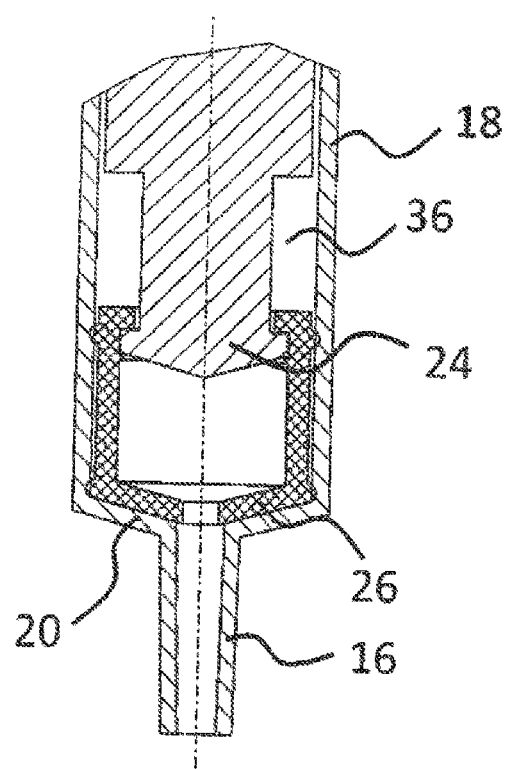
Figure 4:
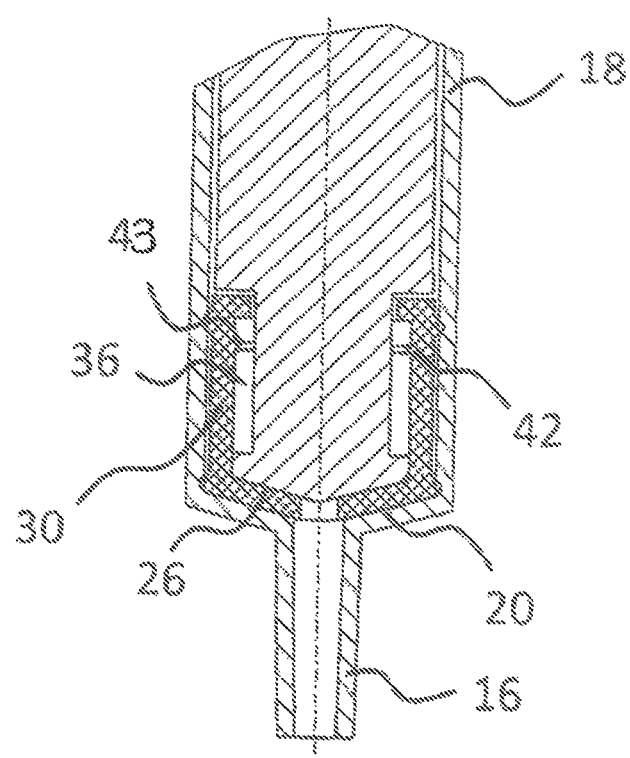
Figure 5:
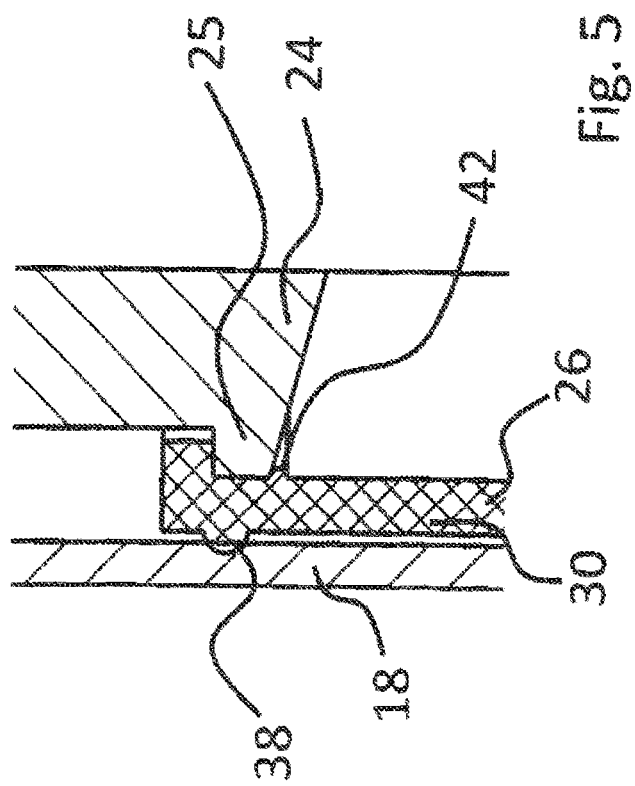
Figure 6:
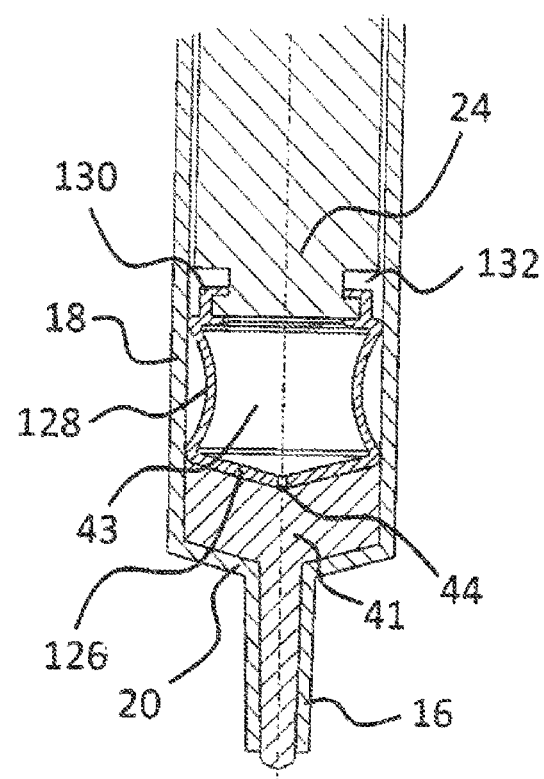
Figure 7:
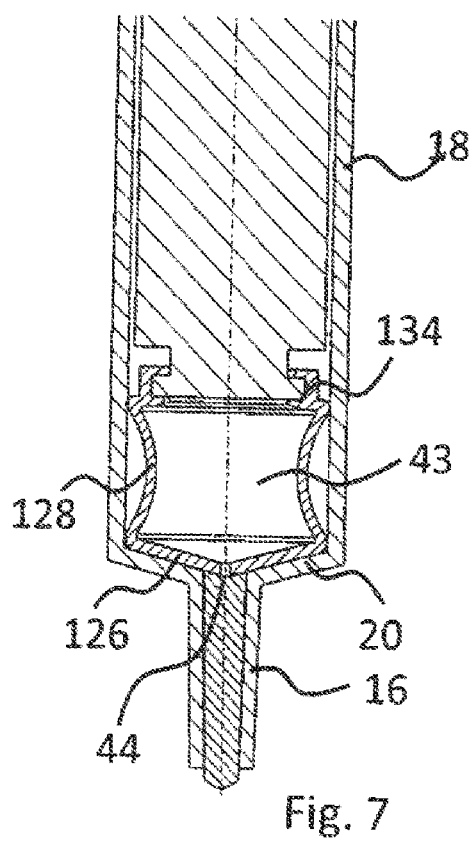
Figure 8:
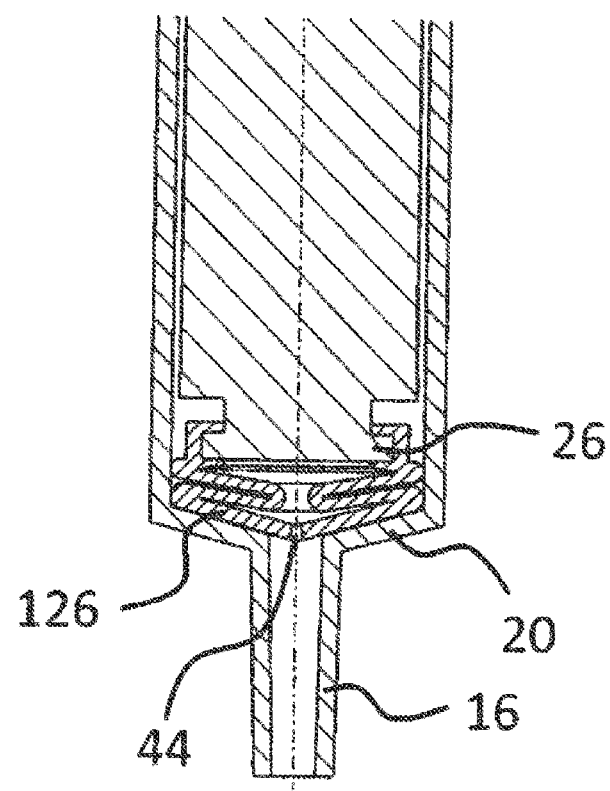
Figure 9:
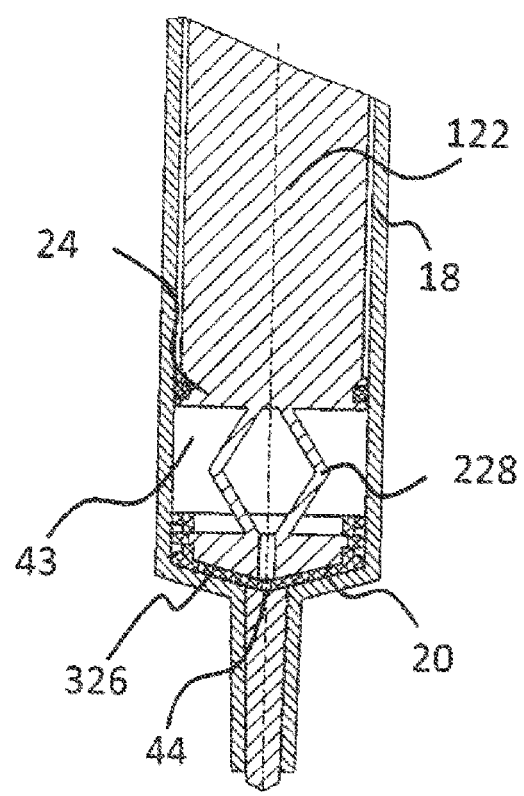
Figure 10:
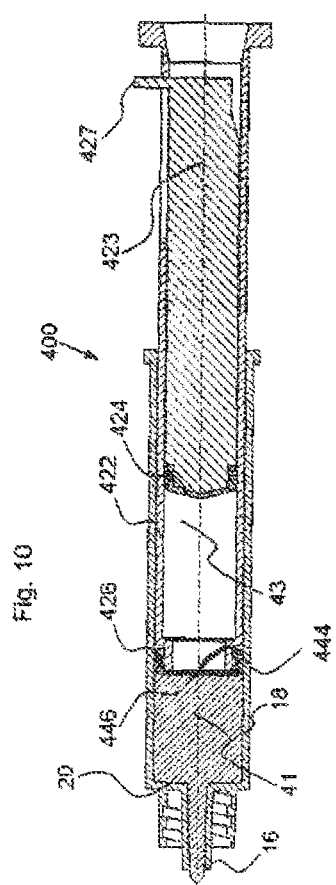
Figure 11:
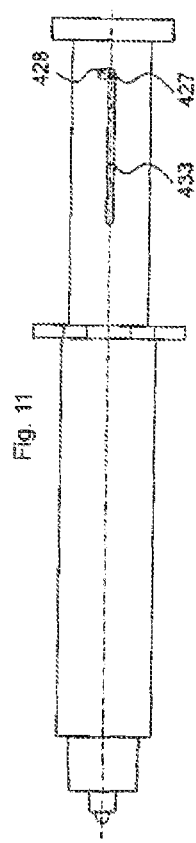
Figure 12:
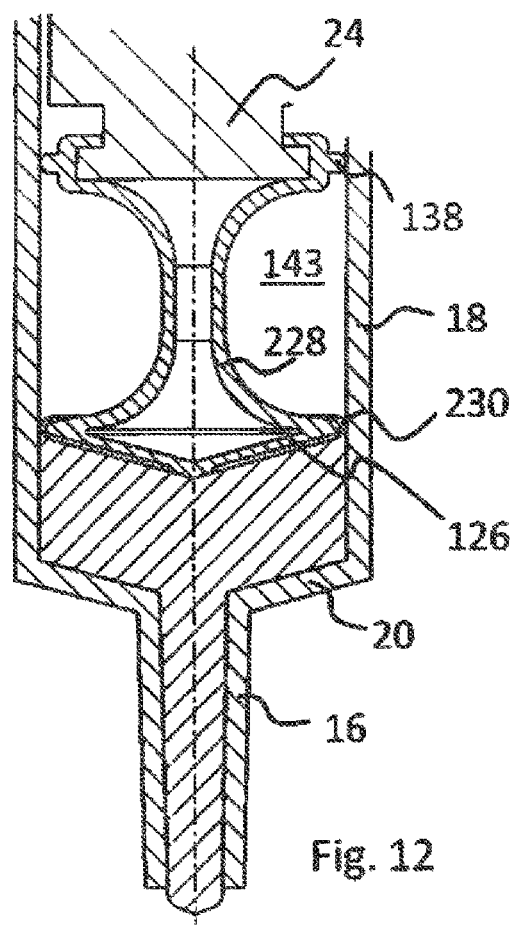
Figure 13:
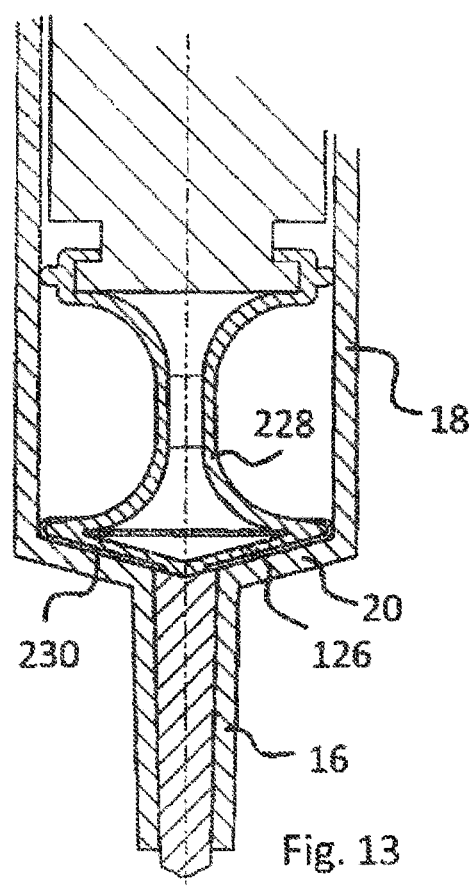
Figure 14:
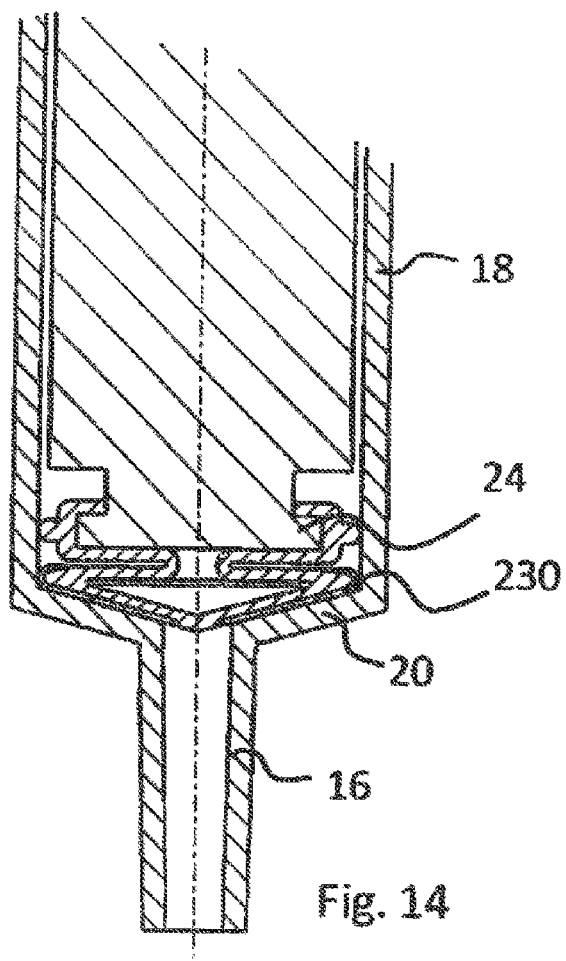

The drawings show:

FIG. 1 a cross-section of a first embodiment of a syringe according to the invention, FIGS. 2-4 cross-sections of the syringe of FIG. 1 in various operating positions, FIG. 5 a cross-section of a portion of the syringe of FIGS. 1-4, FIGS. 6-8 cross-sections of a second embodiment of a syringe in various operating positions, FIG. 9 a cross-section of a third embodiment of a syringe according to invention and FIG. 10 a schematic representation of a longitudinal section of a fourth embodiment of a syringe according to the invention, FIG. 11 the syringe of FIG. 10 from a side view, FIGS. 12-14 an alternative embodiment of a syringe to the second embodiment of FIGS. 6-8, in various working positions and FIGS. 15-22 variants of e syringe of FIGS. 6-8.

FIG. 1 shows a purely schematic illustration of a longitudinal section of a syringe 10, with which first an active substance 12, such as a medicinal agent, is injected, followed by a medium such as sterile air 14, which is to be injected after the first substance in order to fully administer any residual active substance that may be located at least in a neck 16 that extends in the distal region of syringe body 18, and optionally in a cannula, a catheter or some other tubing system that proceeds outward from neck 16. Neck 16 extends outward from a distally extending base wall 20 of cylindrical syringe body 18. Base wall 20 is also referred to as the distal limiting wall.

In place of neck 16, it is also possible for only an opening to be provided, via which the medicinal agent is delivered via suitable connecting means.

A plunger rod 22, which in the embodiment examples is embodied distally as a plunger 24, and which is also referred to as the proximal plunger or the first plunger, can be displaced in the axial direction of syringe body 18. Although in the embodiment example plunger rod 22 is guided slidingly on the inside of cylinder body 18, other known syringe configurations may also be provided.

Proximal plunger 24 is mechanically coupled to a distally extending or second plunger 26, which is embodied as a hollow plunger and comprises an end-face base wall 28 and a circumferential wall 30 embodied as a hollow cylinder. Proximally, that is to say in the unattached end face region, circumferential wall 30 is angled radially inward, i.e. in the direction of the longitudinal axis of plunger 26 and thus in the direction of longitudinal axis 32 of syringe body 18. The edge region is labeled with reference sign 34. Although edge region 34 is preferably embodied as circumferentially angled, the edge may also be angled only in sections. The angled portion or edge 34 extends into a suitably matching axial recess 36 in the circumferential wall of first plunger 24, so that the first plunger 24 can be displaced axially in relation to second plunger 26. Second plunger 26 is sealed peripherally in relation to the inner wall of syringe body 18 (see region 38 in FIG. 5).

As is also clear from the detailed representation according to FIG. 5, section 25 of first plunger 24, which extends within the hollow plunger, i.e. second plunger 26, is held in place via a peripheral bead 42, for example, in order to displace plungers 24, 26 as a single unit as plunger rod 22 is being displaced axially in the direction of neck 16, until the end wall or base wall 28 of second plunger 26 reaches limiting wall 20. With continued application of axial force, the resistance offered by bead 42 against the axial displacement of plunger rod 22 and therefore of first plunger 24 in the axial direction is overcome, allowing first plunger 24 to be displaced axially inside second plunger 26, so that the medium that is present in interior space 43 between plungers 24, 26 is forced out and can exit via an opening 44 provided in base wall 28 of second plunger 26, in order to fully inject any active substance that may still be present in neck 16 and in the cannula, catheter or tubing system connected thereto into a body.

With the axial displacement of plunger rod 22 along with plungers 24, 26 that forma single unit, the active substance that is present in space 41 between the outer side of base wall 28 of second plunger 26 and the inner side of limiting wall 20, referred to as the first volume, is delivered via neck 16 for injection into a body.

The process sequence is illustrated in FIGS. 2, 3 and 4. In the initial state, the drug to be injected is located in the region between the outer surface of base wall 28 of second plunger 26 and syringe body 18 up to neck 16, which forms a first volume 41 (FIG. 2). To administer this drug, plunger rod 22 is displaced axially in the direction of limiting wall 20, without relative movement between the first and second plungers 24, 26. As soon as base wall 28 of second plunger 26 reaches limiting wall 20 (FIG. 3), first plunger 24 is displaced by the continued application of axial force onto plunger rod 22, causing the first plunger to overcome bead 42 in the direction of neck 16, i.e. in the direction of the inner side of limiting wall 28, so that the medium that was previously present in intermediate space 43, referred to as the second volume, is delivered via opening 44 (FIG. 4). Any residual drug that is present in the system comprising syringe 10 and cannula or catheter or tubing system is thereby flushed out. In this case, second volume 43 should preferably be limited or set to a maximum of 0.5 ml, in order to rule out the chances of an air embolism when air is used as the medium. However, saline solution may also be used as the medium, for example.

Flushing ensures that no dead volume of drug will remain in syringe 10 and in any cannula or catheter, or other tubing system that may be connected thereto.

FIGS. 6-8 show another embodiment of the teaching of the invention. Here, the same reference signs as were used in FIGS. 1-5 have been selected for like elements.

In contrast to the embodiment of FIGS. 1-5, the relative displacement of a distally extending second plunger 126 in relation to the first, i.e. proximal plunger 24 is achieved by means of an elastic element such as rubber bellows 128, which ensures the mechanical coupling between the first and second plungers 24, 126. Bellows 128 and second plunger 126, which may be a base-side section of bellows 128, encompasses the space that forms second volume 43, in which a secondary flushing agent such as sterile air may be present. To connect bellows 128 to first plunger 24, bellows 128 has in its proximal region an inwardly angled edge 130, which can be secured and fixed in place in a corresponding recess 132 in first plunger 24. Bellows 128 may be open or closed opposite second plunger 126, as indicated in the drawing (section 134). Regardless of whether it is open or closed, bellows 128 or second plunger 126 is peripherally sealed in relation to the inner wall of syringe body 18. The drug to be injected is provided in the manner described above between this seal and limiting wall 20 of the interior of syringe body 18, and can be delivered by the axial displacement of first plunger 24 in the direction of limiting wall 20. When second plunger 126 abuts the exterior of limiting wall 20, further axial displacement of first plunger 24 will cause bellows 128 to be compressed, thereby delivering the medium encompassed by the bellows, such as sterile air, via opening 44 provided in the second plunger 126, thus enabling the desired secondary injection.

As is clear from FIGS. 6-8, an annular proximally extending region of bellows 128 encompasses a flange-like distally extending section of first plunger 24, in order to prevent an axial displacement of bellows 128 along the circumferential wall of first plunger 24.

The process steps of injection and secondary injection are self-explanatory from a comparison of FIGS. 6-8.

To prevent the proximal or first plunger 24 from being pushed backward following injection of the secondary injection medium, i.e. once second volume 43 has been emptied, as a result of the bias stored in rubber bellows 128, which would result in a suctioning effect that might result in blood being drawn in through neck 16, it is provided that proximal plunger 24 or the elastic element 128 that connects the proximal plunger to distal plunger 126 is locked or fixed in place in some other suitable manner once second volume 43 has been emptied, so that proximal plunger 24 is prevented from sliding back. Locking bellows 128 in the compressed position produces a similar effect.

It is also possible for such fixing to be implemented by the negative pressure that is generated in the inner space delimited between first plunger 24, rubber bellows 128 and distal plunger 126 by the ejection of the secondary injection medium, thereby preventing proximal plunger 24 from being forced backward.

Alternatively or additionally, the opening through which the secondary injection medium is delivered can be sealed by means of a flow check valve, thereby preventing suctioning in and thus a relaxation of bellows 128.

Particularly preferred solutions for preventing proximal plunger 24 from sliding back following secondary injection are illustrated in FIGS. 15-22. These are variants of the syringe according to FIGS. 6-8, and therefore the same reference signs have been used to identify like elements.

The variants of FIGS. 15-22 make it possible to prevent the first or proximal plunger 24 from sliding back as a result of an expansion of the compressed rubber bellows 128 following the secondary injection, i.e. the emptying of second volume 43, which is encompassed by the elastic element, such as rubber bellows 128, that forms second plunger 126. This prevents blood from being drawn from a vein via neck 16, embodied in particular as a Luer's cone, and a tube extending therefrom, for example. This is made possible by the measures described below.

Figure 15:
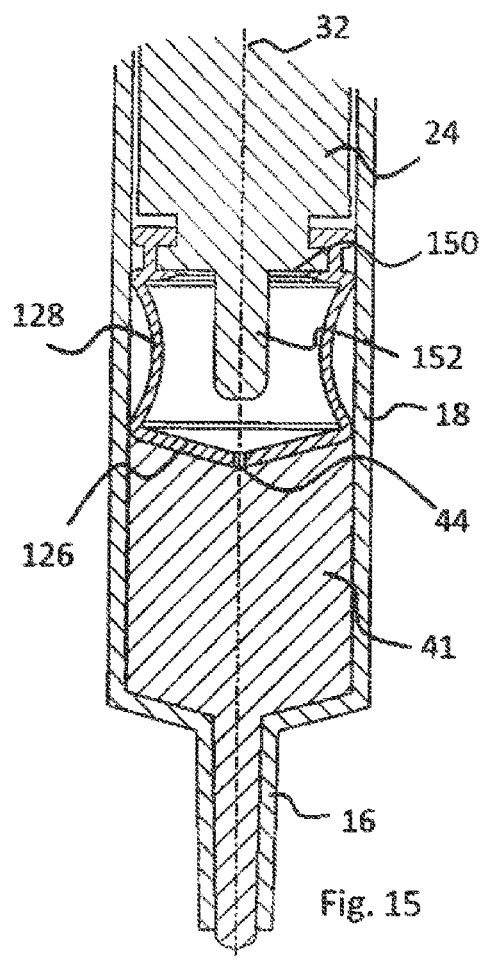
Figure 16:
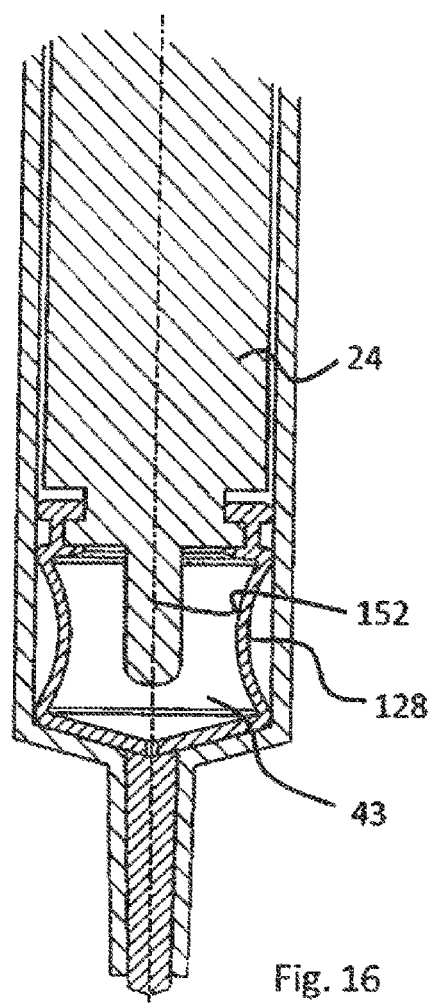
Figure 17:
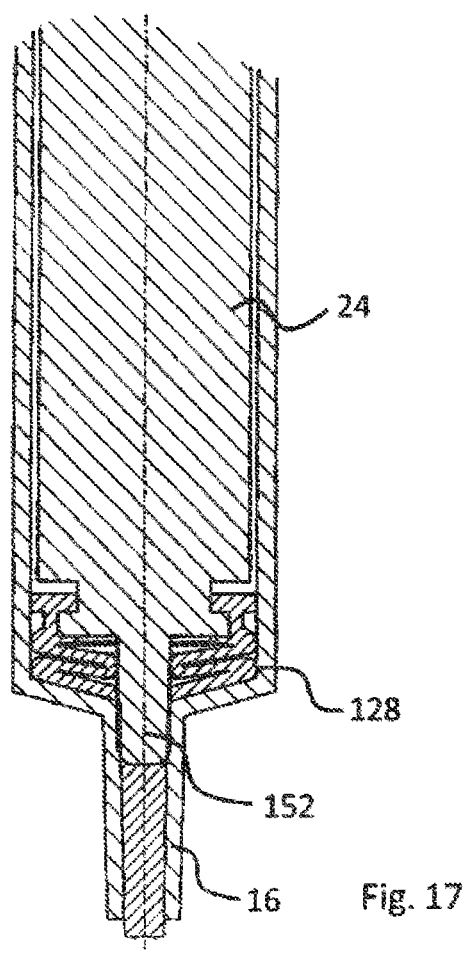

According to the embodiment example of FIGS. 15-17, the invention provides that a projection 152 extending in the direction of longitudinal axis 32 extends outward from proximal plunger 24, specifically from the end face 150 thereof that extends perpendicular to longitudinal axis 32 of cylinder body 18, with the diameter of said projection matching the inner diameter of neck 16 such that when projection 152 penetrates into neck 16 with bellows 128 in a compressed state, a secure clamping is implemented particularly by means of frictional engagement, as shown in FIG. 17. Projection 152 and thus proximal plunger 24 is thereby fixed in place, preventing bellows 128 from expanding; otherwise, negative pressure might build up in neck 16, with the result that blood would be drawn.

FIGS. 15-17 again illustrate the sequence of steps for use of the syringe, i.e., first the injection of the drug for injection, which is held in first volume 41, followed by the injection of the secondary injection medium, such as air, which is held in second volume 43. For this purpose, the distally extending, end-face limiting wall of bellows 128, designated as second plunger 126, has a corresponding opening 44 via which the secondary injection medium can be ejected upon compression of bellows 128.

Figure 18:
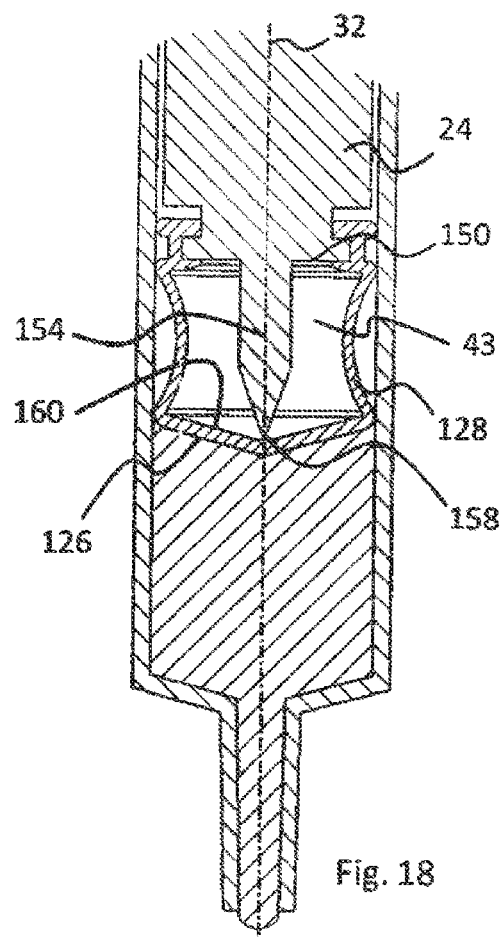
Figure 19:
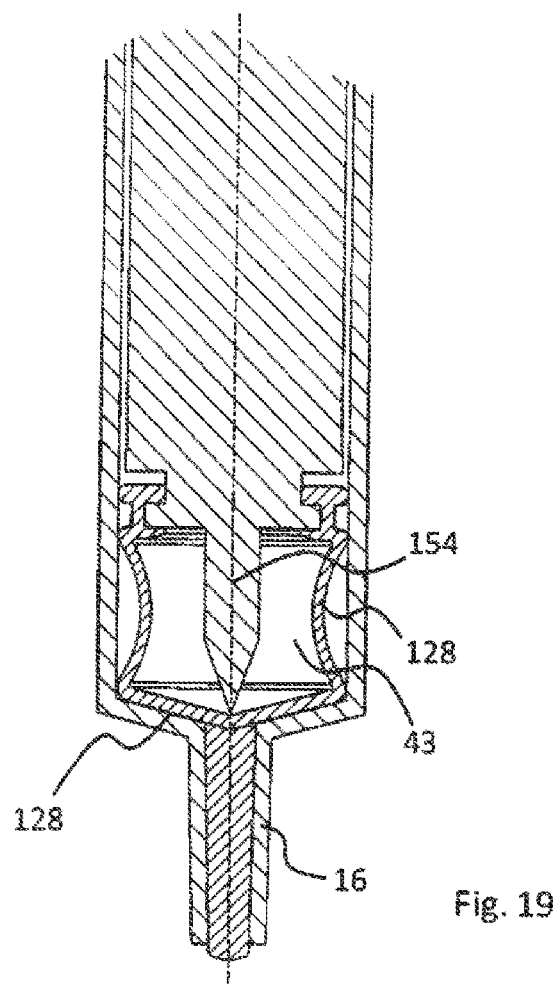
Figure 20:
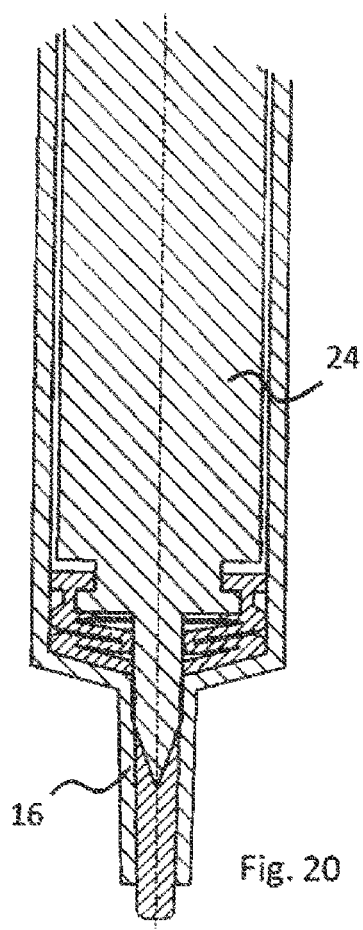

The embodiments of FIGS. 18-20 are different from those of FIGS. 15-17 in that the distal limiting wall of bellows 128 that forms second plunger 126 is completely closed, in other words the secondary injection medium in second volume 43 is completely encompassed by bellows 128 and boundary surface 150 of the first or proximal plunger 24, which extends on the end face thereof. Projection 154, which extends along the longitudinal axis and projects outward from end face 150, differs in terms of its geometry from projection 152 of the embodiment example of FIGS. 15-17 in that the former tapers to a point, that is to say it has a penetrating tip 158, by means of which wall 126 is pierced as bellows 128 is emptied, so that the secondary injection medium held therein is ejected via neck 16. Projection 156 therefore has a longitudinal extension, which corresponds approximately to the distance between boundary surface 150 and inner side 160 of the limiting wall of bellows 128 that forms second plunger 126 when bellows 128 is in the non-compressed state, so that as soon as compression of bellows 128 begins (FIG. 19), tip 158 can penetrate the distal wall of bellows 128, that is to say, second plunger 126. Second volume 43, which is encompassed by bellows 128, is thereby connected to the lumen of neck 16, allowing the secondary injection medium to flow through.

The cross-section of projection 154 according to the embodiment of FIGS. 15-17 is likewise configured to match the inner cross-section of neck 16, so that once second volume 43 has been emptied, i.e. bellows 128 has been compressed, the projection is fixed in place by clamping, and subsequent backward sliding is prevented.

Figure 21:
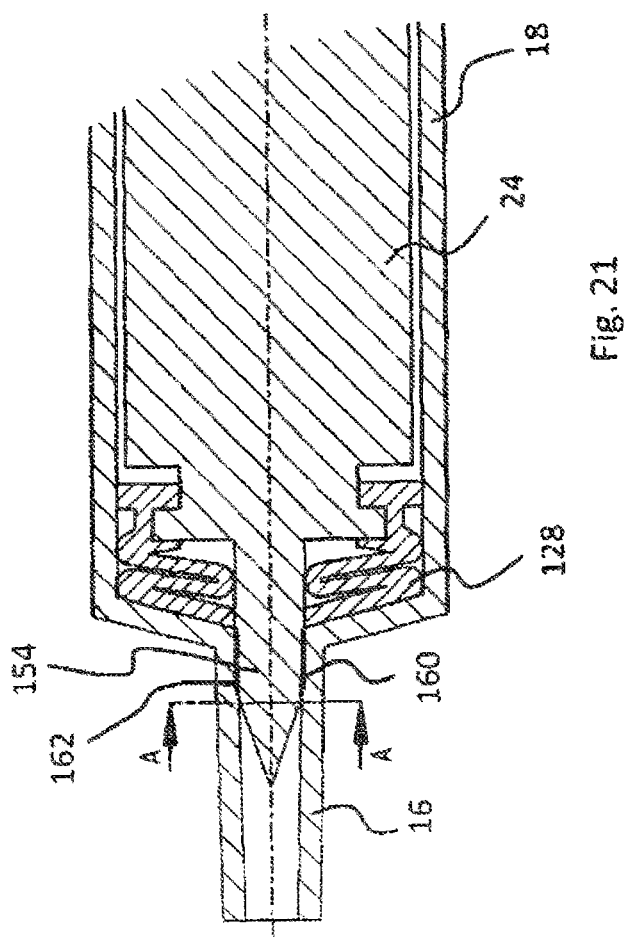
Figure 22:
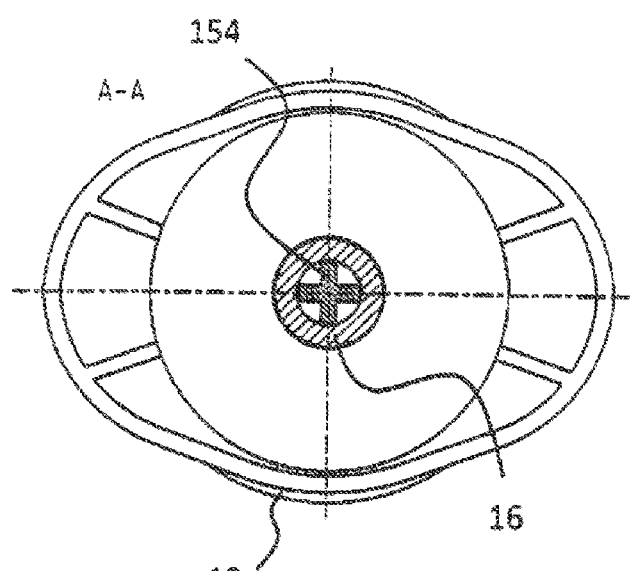

To ensure that the secondary injection medium can flow through neck 16 when projection 152 or 154 enters into neck 16, it is provided according to the illustration of FIGS. 21, 22 that projection 154 shown in the embodiment example has depressions extending lengthwise axially, via which the secondary injection medium can flow into neck 16.

In the embodiment example, projection 154 has a cruciform geometry in cross-section, as is clarified in the sectional illustration A-A in FIG. 22. Irrespective of this, projection 154 can be fixed in place by frictional engagement to the inner wall of neck 46 to prevent proximal plunger 24 from sliding back as a result of the expansion of bellows 128, according to the teaching of the invention.

An alternative embodiment to the syringe according to FIGS. 6-8 is shown in FIGS. 12-14, in which the same reference signs are used for like elements. To avoid repetition, reference is made to the description relating to FIGS. 6-8. In contrast to that embodiment, here an elastically compressible bellows 228, which extends outward from the first plunger 24 and which distally has or forms the second or distal plunger 126, does not encompass or enclose the second volume. Rather, the second volume extends between the outside of bellows 228 and the inside of syringe body 18. This region is labeled with reference sign 143. To prevent the secondary injection medium, such as sterile air, which is held inside second volume 143 from escaping when first plunger 24 is displaced in the direction of limiting wall 20, the proximal region of bellows 228 is sealed relation to syringe body 18. This is symbolized by a peripheral bead 138.

To enable the secondary injection medium that is held in second volume 143 to flow through neck 16 when bellows 228 is compressed (FIG. 14), bellows 228, in its distal region, which abuts the inner surface of the syringe body, has slits, which transition into radially extending recesses 230 in the outer surface of second plunger 126.

As is clear from the sectional illustrations of FIGS. 12 and 13, bellows 228—which corresponds approximately to bellows 128—has the shape in cross-section of two arcuate sections which are concave shape in relation to cylinder body 18 and which transition at their end sides into plungers 24, 126. At its center region, bellows 228 can extend parallel to the longitudinal axis of syringe body 18, as is clear from FIGS. 12 and 13.

To allow air that is present inside bellows 228 to escape when bellows 228 is compressed (FIG. 13, then FIG. 14), corresponding openings can be provided, which extend through the plunger rod or plunger 24 and are not shown here.

Otherwise, the drawings of FIGS. 12-14 are self-explanatory with respect to the functioning of bellows 228 and the geometry thereof.

Proximal plunger 24 can likewise be fixed in place after the secondary injection medium has been ejected from second volume 143\* in the manner previously described above.

A further embodiment of a syringe according to the invention is shown in FIG. 9. In this case, the first or proximal plunger 24, which, in contrast to the embodiment of FIG. 1, extends outward from a plunger rod 122 that is not in contact with the inner wall of syringe body 18, is connected via bridge elements 228 to distal plunger 326, which can then be destroyed or perforated when second plunger 326, which is connected via connecting elements to first plunger 24, reaches boundary surface 20 of syringe body 18 and additional force is applied to plunger rod 122 in the direction of boundary surface 20. The intermediate space (second volume 43) between first plunger 24 and second plunger 326 can thereby be discharged via opening 44, which preferably extends centrally in second plunger 326, into the system that is connected to the syringe.

Opening 44 can be embodied as a slit valve. The same applies to the embodiments of the embodiment examples described above. It is also possible for the opening to be provided with a hydrophobic filter. The option of covering the opening with a membrane that is destroyed—either by a build-up of pressure in second volume 43 or by projections extending from limiting wall 20—is another possibility for allowing the medium present in second volume 43, in particular sterile air, to be secondarily injected as necessary.

The medium required for secondary injection or the active substance itself can also be drawn up in the same manner as in the embodiments of FIGS. 1-8 and 12-14. For drawing up the substances, it is first necessary for first plunger 24 to be displaced in the direction of second plunger 26, 126, thereby decreasing the size of second volume 43 delimited by the second plunger. Plunger rod 22 must then be drawn back in order to enlarge the intermediate space between plungers 24, 26 and 124, 126, allowing the medium to be drawn up. A process sequence in the order of FIG. 4, FIG. 3 or FIG. 8, FIG. 7 or FIG. 13, FIG. 12 is carried out. To fill up first volume 41, second plunger 26, 126 abuts limiting wall 20. The active substance can then be drawn up by displacing plunger rod 22 axially away from limiting wall 20.

FIGS. 10 and 11 show another embodiment of a syringe 400 according to the invention. Merely by way of example, syringe body 18 is shown with neck 16, which may be designed as a Luer lock connector. Held displaceably in syringe body 18 is a plunger rod 422 embodied as a hollow cylinder, in which a first or proximal plunger 424 can be displaced, which is sealed in relation to the inside of hollow plunger 422. A second plunger rod 423, designated as the second actuating element and surrounded coaxially by hollow plunger rod 422, extends outward from the first or proximal plunger 424. Hollow plunger rod 422 has in its distal region a second or distal plunger 426, which is sealed in relation to the inside of syringe body 18. This results in a configuration in which a first volume 41, which can be filled with an active substance, is formed between the outer side of second plunger 426 and the limiting wall 20, which transitions into neck 16 of syringe body 18. Between the first and second plungers 424, 426, a second volume 43 is located, which may be filled with a medium such as sterile air. Second plunger 426 has an opening 444 at its end face.

Syringe 400 according to the invention functions as follows. Once second volume 43 has been filled with sterile air, for example, and first plunger 424 has been locked to hollow plunger 422 via plunger rod 423—for this purpose, a section 427 projecting radially outward from second plunger rod 423 can be provided, which engages in a corresponding recess 428 in the circumferential wall of hollow plunger rod 422—, hollow plunger 422 is displaced axially in the direction of limiting wall 20, so that second plunger 426 rest against the limiting wall. Hollow plunger 422 is then drawn back, so that first volume 41 can be filled with an active substance. This active substance cannot penetrate into second volume 43, since opening 444, which is provided in distal plunger 426 and which is intended to establish a connection with second volume 43, is sealed off by a hydrophobic, air-permeable filter 446. In place of hydrophobic filter 446, opening 444 can also be sealed off by a valve, which ensures that the active substance cannot penetrate into second volume 43, i.e. into the space between plungers 424, 426. Neck 16 is then connected to a cannula or tubing system required for injection. When hollow plunger 422 is then displaced in the direction of limiting wall 20, the active substance is injected, while displacement between the first and second plungers 424, 426, 422 is prevented by the interlocking of hollow plunger 422 and plunger rod 423. Once the active substance has been delivered, second plunger rod 423 is unlocked so that the first or proximal plunger 424 can be displaced in the direction of the second or distal plunger 426. The medium that is held within second volume 43, e.g. sterile air, is then delivered via opening 444, or via filter 446 or a valve, in order to flush out any residual substance that may be present in neck 16 or in the cannula or the tubing system connected thereto.

The invention claimed is:

1. A syringe for the injection of an active substance, comprising:
a cylindrical syringe body having a limiting wall provided in a distal region, which transitions into a neck, or has an opening, via which the active substance can be delivered, two mechanically connected plungers that are axially displaceable in the syringe body, and a first actuating element for mutual displacement of the plungers, wherein, prior to the injection of the active substance, a distal plunger of the two plungers and the limiting wall are spaced from one another and a first volume that is formed thereby is filled with the active substance, wherein the plungers can be displaced as a mechanically coupled unit by the application of force of the first actuating element in the direction of the limiting wall until the distal plunger comes to rest against the limiting wall, or a stop,
wherein, when the plungers are a mechanically coupled unit, mutually facing inner surfaces of the plungers are spaced from one another, and a second volume that is thereby formed is filled with a secondary injection medium, and
wherein, when the distal plunger abuts the limiting wall, a mechanical connection between the plungers can be automatically changed, such that a proximal plunger of the two plungers is displaced in the direction of the distal plunger by a further application of axial force onto the first actuating element,
wherein the displacement of the proximal plunger in the direction of the distal plunger causes the secondary injection medium to push through the distal plunger and/or to flow past the same, and
wherein, after the secondary injection medium is injected, the proximal plunger is prevented from sliding back,
a projection extending outwardly from the proximal plunger in the longitudinal direction of the syringe body,
wherein the proximal plunger is a distal section of a plunger rod that forms the first actuating element,
wherein at least sections of the first actuating element abut against an inner side of the syringe body,
wherein the plunger rod is guided slidingly on the inner side of the syringe body,
wherein the distal plunger is connected to the proximal plunger via an axially compressible hollow body, and wherein the projection is fixable in the neck by frictional engagement with the neck when the hollow body is compressed, and wherein the secondary injection medium is a gas.

2. The syringe according to claim 1, wherein the distal plunger is a hollow plunger having a distally extending base wall and a circumferential wall, which proceeds therefrom and forms a hollow cylinder, and which has an edge region that extends at an end face, at least in sections, radially toward a longitudinal axis of the distal plunger, and wherein said edge region engages in a recess that receives the edge region, and extends in the outer side of the proximal plunger, said recess extending spaced from at least the distal edge of the proximal plunger.

3. The syringe according to claim 1, wherein, as the plungers are being displaced as a unit, they remain spaced from one another by the interaction of the projection that is provided in at least one of the plungers and a matching recess in the other plunger, or by adhesive friction.

4. The syringe according to claim 1, wherein the distal plunger has at least one opening in a distally extending boundary of the distal plunger.

5. The syringe according to claim 4, wherein the at least one opening is sealed off by a valve.

6. The syringe according to claim 5, wherein the valve is selected from the group consisting of a flow check valve, a hydrophobic filter element, and a destructible membrane element.

7. The syringe according to claim 1, wherein the first actuating element is connected to the proximal plunger, into which the displacement forces for displacing the unit comprising the plungers and for displacing the proximal plunger up to the distal plunger are introduced.

8. The syringe according to claim 1, wherein a distal region of the hollow body is the distal plunger.

9. The syringe according to claim 1, wherein the hollow body is prevented, or substantially prevented from expanding, after the hollow body is compressed.

10. The syringe according to claim 1, wherein the hollow body is fixable in the compressed position, and/or the proximal plunger can be fixed in place, when the hollow body is compressed.

11. The syringe according to claim 1, wherein the projection, has a spike-shaped, or pin-shaped geometry, or a geometry that is cruciform, or star-shaped in cross-section, wherein the projection penetrates the hollow body when the hollow body is compressed, in order to produce a connection between the second volume, which is encompassed by the hollow body, and the neck.

12. The syringe according to claim 1, wherein the projection has, on its outer side, at least one depression which extends longitudinally along the projection.

13. The syringe according to claim 1, wherein the proximal plunger is fixed in place, or retained by clamping or frictional engagement of the hollow body and/or the proximal plunger, and/or by a negative pressure that prevails in the space that is encompassed by the plungers, and by the hollow body that connects the plungers.

14. The syringe according to claim 1, wherein the hollow body is a bellows-like hollow body.

15. The syringe according to claim 1, wherein the gas is sterile air.

16. The syringe according to claim 1, wherein the neck is in a form of a Luer cone.

17. A syringe for the injection of an active substance, comprising:

a cylindrical syringe body having a limiting wall provided in a distal region, which transitions into a neck, or has an opening, via which the active substance can be delivered, two mechanically connected plungers that are axially displaceable in the syringe body, and a first actuating element for mutual displacement of the plungers, wherein, prior to the injection of the active substance, a distal plunger of the two plungers and the limiting wall are spaced from one another and a first volume that is formed thereby is filled with the active substance, wherein the plungers can be displaced as a mechanically coupled unit by the application of force of the first actuating element in the direction of the limiting wall until the distal plunger comes to rest against the limiting wall, or a stop, wherein, when the plungers are a mechanically coupled unit, mutually facing inner surfaces of the plungers are spaced from one another, and a second volume that is thereby formed is filled with a medium for secondary injection, and wherein, when the distal plunger abuts the limiting wall, a mechanical connection between the plungers can be automatically changed, such that a proximal plunger of the two plungers is displaced in the direction of the distal plunger by a further application of axial force onto the first actuating element, wherein the displacement of the proximal plunger in the direction of the distal plunger causes the secondary injection medium to push through the distal plunger and/or to flow past the same, wherein, after the secondary injection medium is injected, the proximal plunger is prevented from sliding back, wherein the distal plunger is a hollow plunger having a distally extending base wall and a circumferential wall, which proceeds therefrom and forms a hollow cylinder, and which has an edge region that extends at an end face, at least in sections, radially toward a longitudinal axis of the plunger, and wherein said edge region engages in a recess that receives the edge region and extends in the outer side of the proximal plunger, said recess extending spaced from at least the distal edge of the proximal plunger.

* * * * *

UNITED STATES PATENT AND TRADEMARK OFFICE
CERTIFICATE OF CORRECTION

PATENT NO. : 10,639,429 B2  
APPLICATION NO. : 15/033691  
DATED : May 5, 2020  
INVENTOR(S) : Hans Haindl et al.

Page 1 of 1

It is certified that error appears in the above-identified patent and that said Letters Patent is hereby corrected as shown below:

On the Title Page

Item (71) Applicant:
"SFM MEDICAL DEVICES GMBH, Wächtersbach (DE)"
Should read:
--Hans Haindl, Wennigsen (DE)--.

Signed and Sealed this
Eighth Day of December, 2020

Andrei Iancu
*Director of the United States Patent and Trademark Office*